(12) United States Patent
Yan

(10) Patent No.: US 11,678,787 B2
(45) Date of Patent: Jun. 20, 2023

(54) SOFT ENDOSCOPY DEVICE

(71) Applicant: ANQING MEDICAL CO., LTD, Shanghai (CN)

(72) Inventor: Hang Yan, Shanghai (CN)

(73) Assignee: ANQING MEDICAL CO., LTD, Shanghai (CN)

( * ) Notice: Subject to any disclaimer, the term of this patent is extended or adjusted under 35 U.S.C. 154(b) by 0 days.

(21) Appl. No.: 17/624,262

(22) PCT Filed: Mar. 29, 2021

(86) PCT No.: PCT/CN2021/083563
§ 371 (c)(1),
(2) Date: Dec. 31, 2021

(87) PCT Pub. No.: WO2022/057233
PCT Pub. Date: Mar. 24, 2022

(65) Prior Publication Data
US 2022/0346630 A1    Nov. 3, 2022

(30) Foreign Application Priority Data

Sep. 17, 2020   (CN) .......................... 202010978469.8

(51) Int. Cl.
*A61B 1/00* (2006.01)
*A61B 1/005* (2006.01)
(Continued)

(52) U.S. Cl.
CPC .......... *A61B 1/00066* (2013.01); *A61B 1/005* (2013.01); *A61B 1/00105* (2013.01);
(Continued)

(58) Field of Classification Search
None
See application file for complete search history.

(56) References Cited

U.S. PATENT DOCUMENTS

| 10,736,491 B2 * | 8/2020 | Truckai .............. A61B 18/1485 |
| 10,918,263 B2 * | 2/2021 | Cheng .................... A61B 1/126 |
| 2016/0143512 A1 | 5/2016 | Cheng et al. |

FOREIGN PATENT DOCUMENTS

| CN | 2719215 Y | 8/2005 |
| CN | 103181793 A | 7/2013 |

(Continued)

*Primary Examiner* — Timothy J Neal
(74) *Attorney, Agent, or Firm* — Bayramoglu Law Offices LLC

(57) ABSTRACT

A soft endoscopy device includes an endoscope body structure, a camera assembly and an instrument adapter structure. The endoscope body structure includes a bendable flexible inserting portion and a handle portion connected to one end of the flexible inserting portion, the handle portion being provided with a first access portion, and the flexible inserting portion being internally provided with a first passage. The first access portion is directly or indirectly connected with the first passage. When the camera assembly accesses the first access port, at least a part of the camera assembly extends into the first passage. When the instrument adapter structure accesses the first access port, the first instrument extends into the first passage. According to the soft endoscopy device, the functions of the passages and the access ports are expanded by introducing the instrument adapter structure and by multiplexing the passages and the access ports.

11 Claims, 11 Drawing Sheets

(51) Int. Cl.
*A61B 1/018* (2006.01)
*A61B 1/04* (2006.01)
*A61B 1/07* (2006.01)

(52) U.S. Cl.
CPC .......... *A61B 1/00124* (2013.01); *A61B 1/018* (2013.01); *A61B 1/04* (2013.01); *A61B 1/07* (2013.01)

(56) References Cited

FOREIGN PATENT DOCUMENTS

| | | |
|---|---|---|
| CN | 108392717 A | 8/2018 |
| CN | 109310289 A | 2/2019 |
| CN | 110101354 A | 8/2019 |
| CN | 110215180 A | 9/2019 |
| CN | 210300920 U | 4/2020 |
| CN | 111184496 A | 5/2020 |
| CN | 111202487 A | 5/2020 |
| CN | 111990947 A | 11/2020 |

* cited by examiner

SOFT ENDOSCOPY DEVICE

CROSS REFERENCE TO THE RELATED APPLICATIONS

This application is the national phase entry of International Application No. PCT/CN2021/083563, filed on Mar. 29, 2021, which is based upon and claims priority to Chinese Patent Application No. 202010978469.8, filed on Sep. 17, 2020, the entire contents of which are incorporated herein by reference.

TECHNICAL FIELD

The invention relates to the field of medical instruments, and more specifically, to a soft endoscopy device.

BACKGROUND

In recent years, endoscopes and related surgical instruments are used extensively in the field of minimally invasive diagnosis and treatment. With the rapid development of minimally invasive medical technology, higher requirements are put forward for endoscopes. According to the sites at which the endoscope arrives, the endoscope can be classified into a neural endoscope, a cysto-urethroscope, a resectoscope, a laparoscope, an arthroscope, a nasal endoscope, a laryngoscope, and so on. According to the bending degree of the head of the endoscope, the endoscope can be divided into a soft endoscope and a rigid endoscope.

In the prior art, the soft endoscope may include a camera assembly and an endoscope body structure. Meanwhile, the endoscope body structure may be provided with an instrument access port, a camera access port, an instrument passage and a camera passage, wherein an instrument may be accessed by the instrument access port and the instrument passage, and the camera assembly may be accessed by the camera access port and the camera passage. With this structure, the instruments are inserted into the instrument passage by way of alternating in sequence when a doctor has to operate a variety of instruments, which tremendously increases the time and difficulty in operation, and may not possibly achieve a combined operation of a large number of instruments.

Apparently, in the above solution, the instrument can only be accessed by the instrument access port and the instrument passage, while the requirement of simultaneously accessing two kinds of instruments cannot be realized. Furthermore, the positions of the inserted instruments cannot be indicated.

SUMMARY

The present invention provides a soft endoscopy device to solve the problem of not being capable of simultaneously accessing two instruments, and further, to solve the problem of how to indicate the positions of the inserted instruments precisely.

According to a first aspect of the present invention, a soft endoscopy device is provided, which includes an endoscope body structure, a camera assembly and an instrument adapter structure, wherein the endoscope body structure includes a bendable flexible inserting portion and a handle portion connected to one end of the flexible inserting portion, the handle portion being provided with a first access port, and the flexible inserting portion being internally provided with a first passage; the first access port being directly or indirectly connected with the first passage;

the first access port being matched with the camera assembly, and when the camera assembly accesses the first access port, at least part of the camera assembly extending into the first passage; and the first access port being further matched with the instrument adapter structure, and when the instrument adapter structure accesses the first access port and the instrument adapter structure is equipped with a first instrument, the first instrument extending into the first passage.

Optionally, the instrument adapter structure includes a first grip, and the first grip being internally provided with an instrument passage for the first instrument to penetrate through.

Optionally, the handle portion is further provided with a second access port for accessing a second instrument, a second passage for the second instrument to extend into penetrating through the flexible inserting portion, and the second access port being directly or indirectly connected with the second passage.

Optionally, the handle portion is further internally provided with a first electrical interface; when the camera assembly accesses the handle portion internally, the camera assembly is conductively inserted into the first electrical interface; and the instrument adapter structure is provided with an electrical interface protective portion; when the instrument adapter structure accesses the handle portion internally, the electrical interface protective portion is docked with the first electrical interface.

Optionally, the endoscope body structure further includes an external connecting portion located outside the handle portion, the electrical interface being directly or indirectly electrically connected with the external connecting portion, and when the camera assembly is inserted into the first electrical interface, the camera assembly being capable of transmitting electrical energy and/or a signal to the external connecting portion through the first electrical interface.

Optionally, the endoscope body structure further includes a circuit board and a first electrical wire, the circuit board being electrically connected with the first electrical interface, and the circuit board being connected with the external connecting portion via the first electrical wire to transmit the electrical energy and/or the signal by using the first electrical wire; and the circuit board being located in the handle portion, and the first electrical wire penetrating through a wire via disposed at the handle portion.

Optionally, the flexible inserting portion includes a bending rod, a head module and an optical indication module extending to the head module, one end of the bending rod being connected with the handle portion, and the other end of the bending rod being connected with the head module; both the first passage and the second passage for the second instrument to penetrate through penetrating through the bending rod, and both the first passage and the second passage extending into the head module; and the optical indication module being used to externally indicate a position of the instrument extending into the passage.

Optionally, the head module is internally provided with a first head passage, a second head passage, a lighting component, and at least one head optical fiber passage, the optical indication module including an illumination optical fiber penetrating the head optical fiber passage, and the handle portion being provided with an observation window;

the first passage being docked with an inlet of the first head passage, the second passage being docked with an inlet of the second head passage, an optical import end of the head optical fiber passage extending to the first channel of the first head passage or the second head passage, and an instrument accessing the first head passage or the second head passage being capable of shielding the optical import end of the corresponding head optical fiber passage;

when one end of the head optical fiber passage is not shielded by the accessed instrument, a first end of the illumination optical fiber being capable of collecting an optical signal directly or indirectly transmitted by the lighting component; the illumination optical fiber further being capable of conducting the optical signal to a second end of the illumination optical fiber, and the second end of the illumination optical fiber extending into the handle portion and located at an inner side of the observation window.

Optionally, the camera assembly includes a camera encapsulation portion, a conducting rod, a second grip, a second electrical interface disposed at the second grip and a second electrical wire;

at least a part of a rod segment of the conducting rod being bendable, one end of the conducting rod being connected with the second grip, and the camera encapsulation portion being disposed at the other end of the conducting rod; the second electrical wire penetrating through the conducting rod and the second grip, one end of the second electrical wire being directly or indirectly connected with the camera encapsulation portion, and the other end of the second electrical wire being directly or indirectly connected with the second electrical interface; and when the camera assembly accesses the first access port, the second electrical interface being inserted into the first electrical interface in the handle portion, and the conducting rod extending into the first passage.

Optionally, the second electrical interface is a Type C male connector, and the first electrical interface is a Type C receptacle.

In the soft endoscopy device provided by the present invention, by introducing the instrument adapter structure, the first instrument may be accessed to the soft endoscope device after being assembled to the instrument adapter structure, while the passage and the access port that access the first instrument may use the passage and access portion of the camera assembly (i.e., the first passage and the first access port) repeatedly. It can be seen that, according to the present invention, by the instrument adapter structure and using the passage and the access port repeatedly, an introduction passage of the first instrument is formed. Compared with a solution where the passage and the access port may only be used for accessing the camera assembly, the present invention expands the functions of the passage and the access port, so as to realize a new accessing way of the instrument, thereby providing a basis for accessing double instruments. In a further solution, by combined usage of the second passage, the second access port, the first passage and the first access port, accessing and using double instruments can be realized, thereby facilitating enriching the functions of the soft endoscopy device and providing possibilities of combined usage of a variety of instruments to complete more complicated operations for the doctor. Meanwhile, under the concept of the present invention, accessing double instruments does not require occupation of more radial space (e.g., the passage may not be provided additionally), and can effectively control the size of the outer diameter of the endoscopy device.

In a further optional solution, by configuring the electrical interface protective portion for the instrument adapter structure, the electrical interface may be effectively protected, e.g., the electrical interface may be protected from water or other foreign objects.

In a further optional solution, by the illumination optical fiber and the corresponding head optical fiber passage, the introduction and the conduction of the optical signals may be realized; further, by observing through the observation window, a situation where whether the instrument is inserted into the corresponding position of the head module may be observed, wherein specifically, it is indicated that the optical import end of the head fiber optical passage has not been shielded and then it can be considered that the corresponding instrument has not been inserted into place when exported optical signals are observed, and it is indicated that the optical import end of the head fiber optical passage has been shielded and then it can be considered that the corresponding instrument has been inserted into place (or substantially inserted into place) when exported optical signals are not observed (or the observed light is weak).

BRIEF DESCRIPTION OF THE DRAWINGS

To clearly describe the technical solutions in the embodiments of the present invention or in the prior art, accompanying drawings required to describe the embodiments or the prior art are briefly described below. It is obvious that the accompanying drawings described below are only some embodiments of the present invention. It is apparent to those of ordinary skill in the art that other drawings may be further obtained based on the accompanying drawings without inventive effort.

DESCRIPTION OF REFERENCE NUMERALS

Figure 1A:
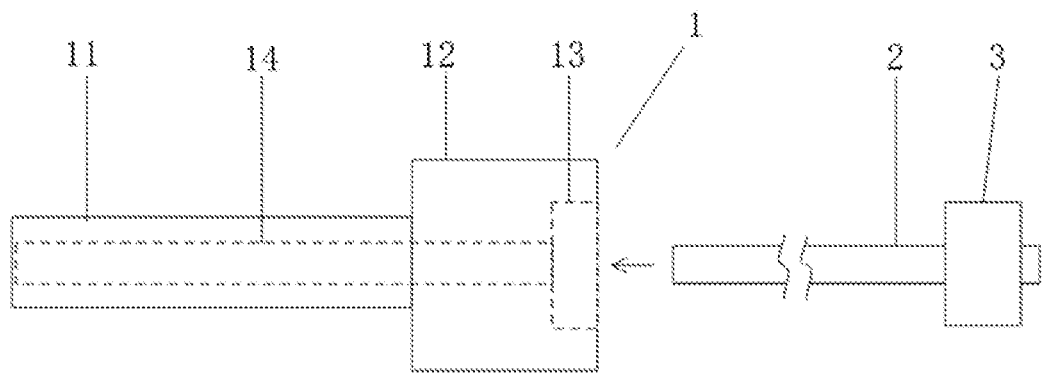
FIG. 1a is a construct diagram one of a soft endoscopy device according to an embodiment of the present invention.
Figure 1B:
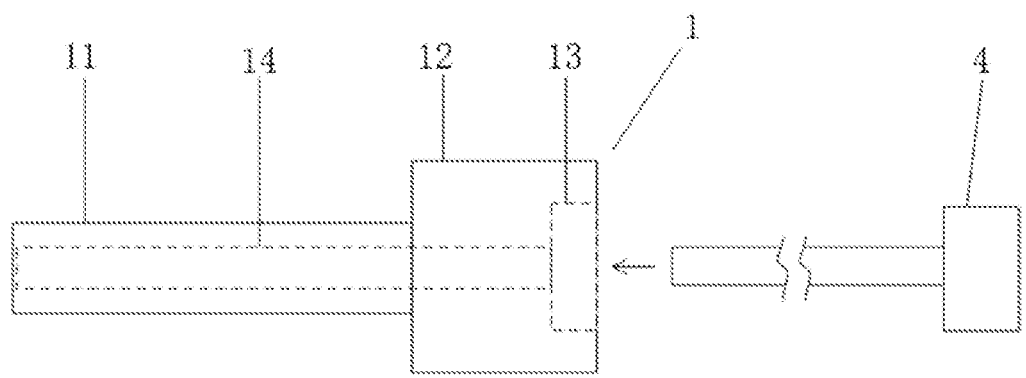
FIG. 1b is a construct diagram two of the soft endoscopy device according to an embodiment of the present invention.

1—endoscope body structure;
11—flexible inserting portion;
111—head module;
112—first head passage;
113—second head passage;
114—head optical fiber passage;
115—rear end inserting cavity;
116—lighting component;
12—handle portion;
13—first access port;
14—first passage;
15—second access port;
16—second passage;
17—external connecting portion;
18—first electrical wire;
19—optical indication module;
191—illumination optical fiber;
2—first instrument;
3—instrument adapter structure;
31—first grip;
32—electrical interface protective portion;
33—export interface;
34—import interface;
4—camera assembly;
41—second grip;
411—grip head;
412—elastic compensation structure;
4121—elastic component;
4122—component cover;
4123—component sleeve;
4124—component seat;
42—second electrical interface;
43—camera encapsulation portion;
44—conducting rod;
45—second electrical wire;
46—Second circuit board;
5—second instrument;
6—sterile isolation cover;

DETAILED DESCRIPTION OF THE EMBODIMENTS

Clear and intact description will be made on technical schemes in the embodiments of the present invention below in combination with drawings in the embodiments of the present invention. Obviously, the described embodiments are merely a part of embodiments of the present invention and are not all the embodiments. Based on the embodiments of the present invention, all the other embodiments obtained by those of ordinary skill in the art without inventive effort are within the scope of the present invention.

Terms "first", "second", "third", "fourth", and the like (if any) in the specification and claims of the present invention and the foregoing accompanying drawings are used to distinguish similar objects, but do not need to be used for describing a specific sequence or an order. It should be understood that data used in this way can be interchanged under appropriate circumstances, so that the embodiments of the present invention described herein can be implemented in an order other than those illustrated or described herein. In addition, terms "including", "having", and any variations thereof are intended to cover non-exclusive inclusions, for example, processes, methods, systems, products, or devices that contain a series of steps or units need not be limited to those clearly listed steps or units, but may include other steps or units not explicitly listed or inherent to these processes, methods, products, or devices.

The technical solutions of the present invention are described in detail below with reference to the specific embodiments. The following several embodiments may be combined with each other, and a same or similar concept or process may not be described again in some embodiments.

With reference to FIGS. 1a, 1b, 2a and 2b, a soft endoscopy device includes an endoscope body structure 1, a camera assembly 4 and an instrument adapter structure 3.

The endoscope body structure 1 may be a disposable endoscope body structure 1, and the camera assembly 2 may be the camera assembly 2 capable of being used repeatedly. The endoscope body structure 1 may specifically be a sterile product, which may be discarded after being used; the camera assembly 2 should be disinfected (in the form of alcohol wipe or plasma sterilization) before the operation is carried out.

In an embodiment of the present invention, the endoscope body structure 1 includes a bendable flexible inserting portion 11 and a handle portion 12 connected to one end of the flexible inserting portion 11, the handle portion 12 is provided with a first access port 13, and the flexible inserting portion 11 is provided with a first passage 14 penetrating through it; the first access port 13 is directly or indirectly connected with the first passage 14.

The endoscope body structure 1 may be understood to be configured with the flexible inserting portion 11 and the handle portion 12, and may be any structure that can provide an isolated environment for the accessed camera assembly and the accessed instrument. Also, the endoscope body structure may be described as an endoscope, an outer sheath and the like, and any construct that is applied to the endoscope body, the endoscope sheath and the outer sheath may be applied to the present embodiment for realizing the functions of the endoscope body structure 1. The flexible inserting portion 11 may be understood as a construct used for inserting and capable of being bent flexibly, wherein a part thereof may be formed by connecting rigid couplings or soft couplings, or may be formed by carving out the corresponding patterns on the rigid or soft couplings.

The camera assembly 2 may be understood to be any structure that can realize endoscopy through the image acquisition. The camera assembly 2 may access the endoscope body structure 1, or may be withdrawn from the endoscope body structure. Therefore, in an embodiment of the present invention, with reference to FIG. 1b, the first access port 13 is matched with the camera assembly 4, wherein being matched with means that the size, the shape and the like of the camera assembly 4 may be suitable for accessing the first access port 13. When the camera assembly 4 accesses the first access port 13, at least a part of the camera assembly 4 extends into the first passage 14.

In an embodiment of the present invention, with reference to FIG. 1a, the first access port 13 is further matched with the instrument adapter structure 3, wherein being further matched with means that the instrument adapter structure 3 and the instrument assembled to the instrument adapter structure 3 may be suitable for accessing the first access port 13, and the first instrument 2 extends into the first passage 14 when the instrument adapter structure 3 accesses the first access port 13 and the instrument adapter structure 3 is assembled with the first instrument 2.

The first instrument may be any instrument that can access the endoscope body structure; for example, any one of the following may be used as the first instrument: an electrocoagulation instrument, a cutting instrument, a clamping instrument, a snare instrument, etc.

In the above solution, by introducing the instrument adapter structure, the first instrument may be accessed to the soft endoscope device after being assembled to the instrument adapter structure, while the passage and the access port that access the first instrument may use the passage and the access port of the camera assembly (i.e., the first passage and the first access port) repeatedly. It can be seen that, according to the present invention, by the instrument adapter structure and using the passage and the access port repeatedly, an introduction path of the first instrument is formed. Compared with a solution where the passage and the access port may only be used for accessing the camera assembly, the present invention expands the functions of the passage and the access port, so as to realize a new way of accessing the instrument, thereby providing a basis for accessing double instruments.

Figure 2A:
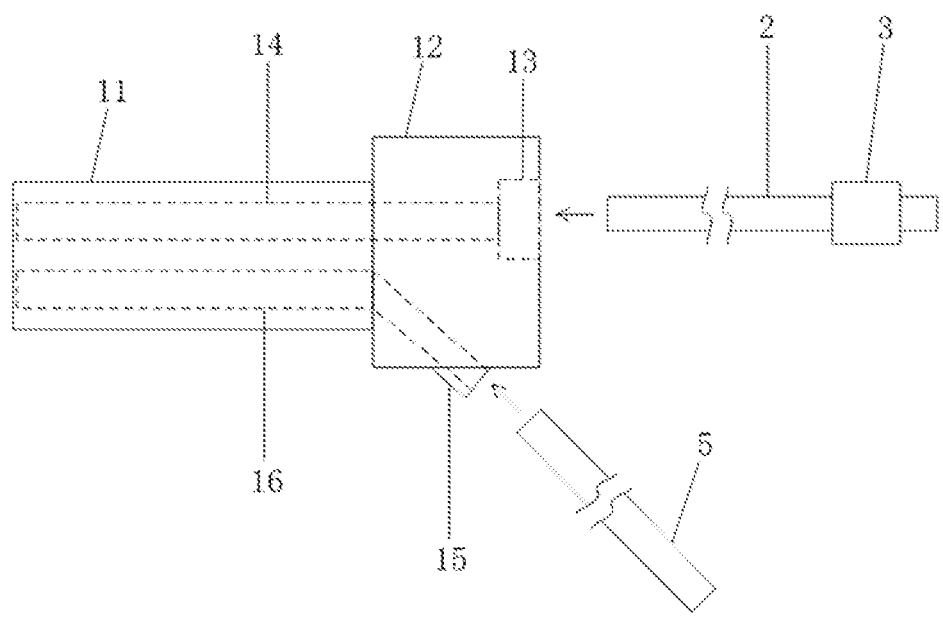
FIG. 2a is a construct diagram three of the soft endoscopy device according to an embodiment of the present invention.
Figure 2B:
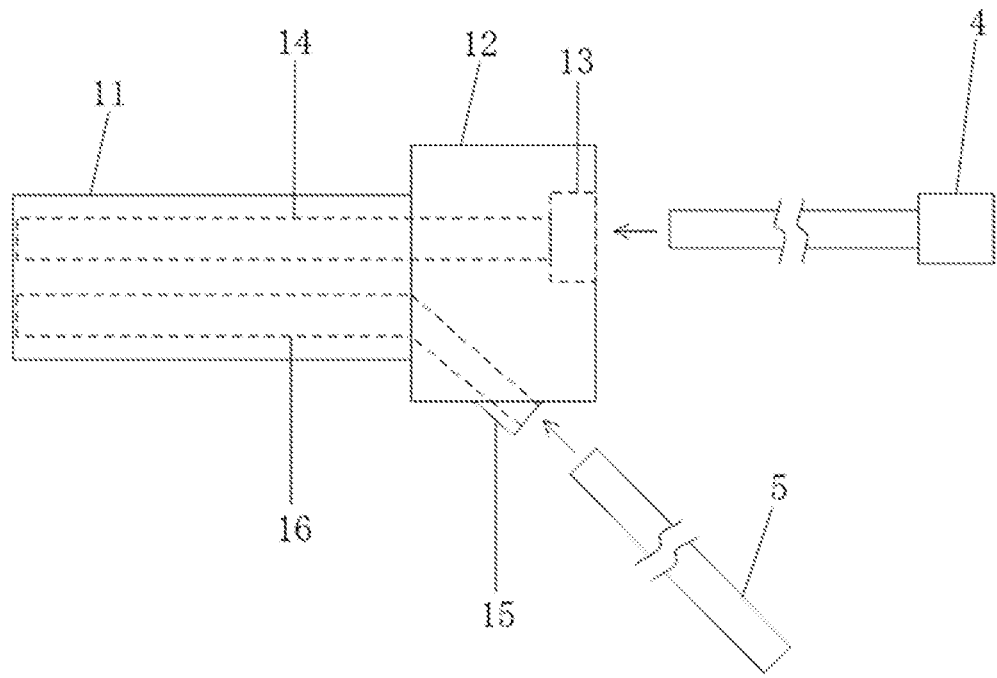
FIG. 2b is a construct diagram four of the soft endoscopy device according to an embodiment of the present invention.
Figure 3:
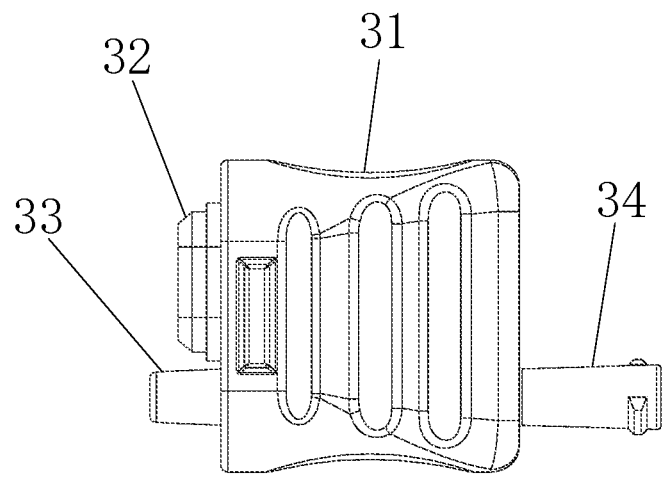
FIG. 3 is a structural diagram one of an instrument adapter structure according to an embodiment of the present invention.
Figure 4:
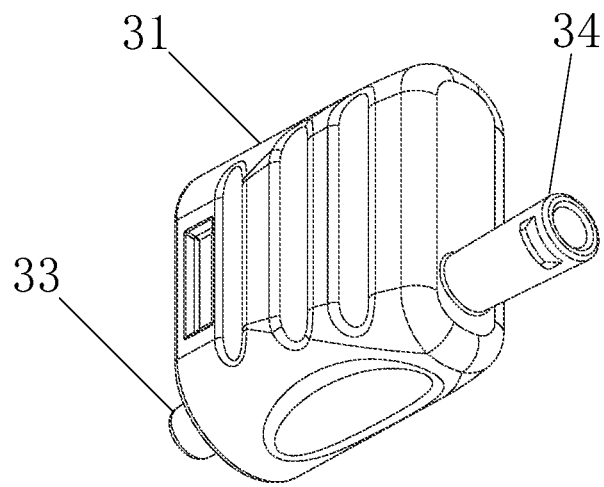
FIG. 4 is a structural diagram two of the instrument adapter structure according to an embodiment of the present invention.
Figure 5:
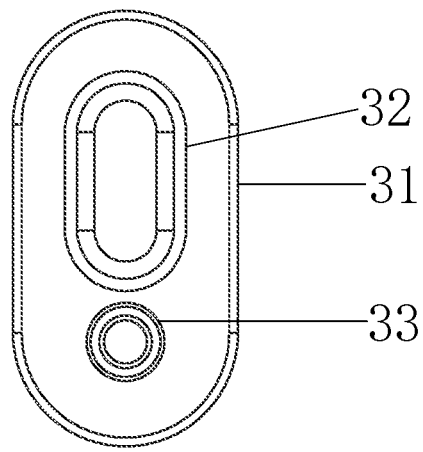
FIG. 5 is a structural diagram three of the instrument adapter structure according to an embodiment of the present invention.
Figure 6:
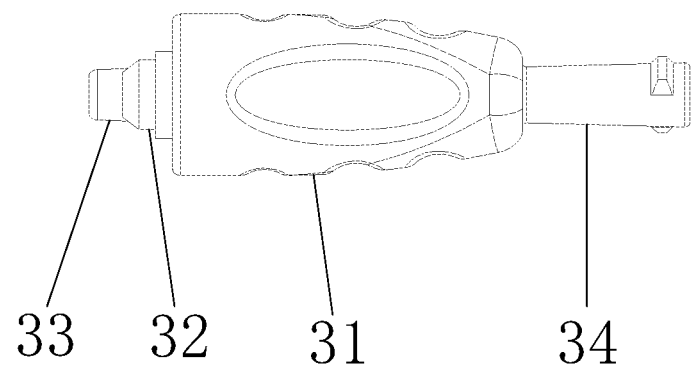
FIG. 6 is a structural diagram four of the instrument adapter structure according to an embodiment of the present invention.

In a further solution, with reference to FIGS. 2a and 2b, the handle portion 12 is further provided with a second access port 15 for accessing a second instrument 5, the flexible inserting portion 11 is also provided with a second passage 16 penetrating through it for the second instrument 5 to extend into, and the second access port 15 is directly or indirectly connected with the second passage 16.

For example, the second instrument 5 may be any one of the following: an electrocoagulation instrument, a cutting instrument, a clamping instrument, a snare instrument, etc.

Regardless of the type of the first instrument and the second instrument, they do not depart from the scope of the embodiments of the present invention.

The first passage and the second passage involved above may be formed by using independent tube bodies, which may penetrate through the flexible inserting portion; in some solutions, the first passage and the second passage may also be formed in the flexible inserting portion without configuring the tube bodies independently. Meanwhile, the first passage and the first access port, and the second passage and the second access port may be directly or indirectly connected (e.g., via an intermediate connecting structure) with each other.

In the above solution, accessing and using the double instruments is achieved, so that the functions of the soft endoscopy device are enriched, and possibilities of combined usage of a variety of instruments to complete more complicated operations are provided for the doctor. Meanwhile, under the concept of the present invention, accessing double instruments does not require occupation of more radial space (e.g., the passage may not be provided additionally), and the effect of effectively controlling the size of the outer diameter of the endoscopy device may be generated.

In addition, the passage for arranging the instrument is not limited to the above double passages. No matter how many passages are used, as long as two of the passages meet the above description, they will not depart from the scope of the embodiments of the present invention.

It can be seen that, in practice, when the detachable camera assembly accesses the disposable endoscope body structure, there is no obvious structural difference from the ordinary soft endoscope; when the detachable camera assembly is withdrawn from the endoscope body structure, the vacant passages may form a double instrument passage, which also provides the possibility for doctors to use multiple instruments in combination to complete more and more complicated operations, while effectively controlling the size of the outer diameter of the endoscope.

In an embodiment, with reference to FIGS. 3 to 6, the instrument adapter structure 3 includes a first grip 31, and the first grip 31 being internally provided with an instrument passage for the first instrument 2 to penetrate through.

Further, one end of the first grip 31 may be provided with an import interface 34, and the other end thereof may be provided with an export interface 33; the first instrument 2 may be imported to penetrate through the instrument passage through the import interface 34, and the instrument passage involved above may be connected with the import interface 34 and the export interface 33 respectively.

The import interface 34 and the export interface 33 may be a structure protruded from the first grip 31. For example, a caliber of an end of the import interface 34 close to the first grip 31 may be much smaller than that of an end thereof deviated from the first grip 31. Meanwhile, the export interface 33 may also be a structure capable of being positioned and assembled to the handle portion; for example, the handle portion may be provided with a docking matching portion for docking with and positioning with the export interface 31.

Moreover, the export interface 33 may adopt an elastic compensation structure, which, for example, may be matched with the elastic compensation structure 412 in the second grip 41 hereinafter.

In an embodiment, the handle portion is further internally provided with a first electrical interface (not shown); when the camera assembly 4 accesses the handle portion 12 internally, the camera assembly 4 is conductively inserted into the first electrical interface.

Correspondingly, the instrument adapter structure 3 is provided with an electrical interface protective portion 32, i.e., an end of the first grip 31 (the end provided with the export interface) is provided with the electrical interface protective portion 32; when the instrument adapter structure 3 accesses the handle portion 12 internally, the electrical interface protective portion 32 is docked with the first electrical interface. In this solution, by configuring the electrical interface protective portion for the instrument adapter structure, the electrical interface may be effectively protected, e.g., the electrical interface may be protected from being affected by water or other foreign matters.

In practice, the instrument adapter structure is configured to access the connecting ports of other instruments and protect the electrical interface in the form of TypeC, for example, from contacting water when the camera assembly is withdrawn.

Figure 7A:
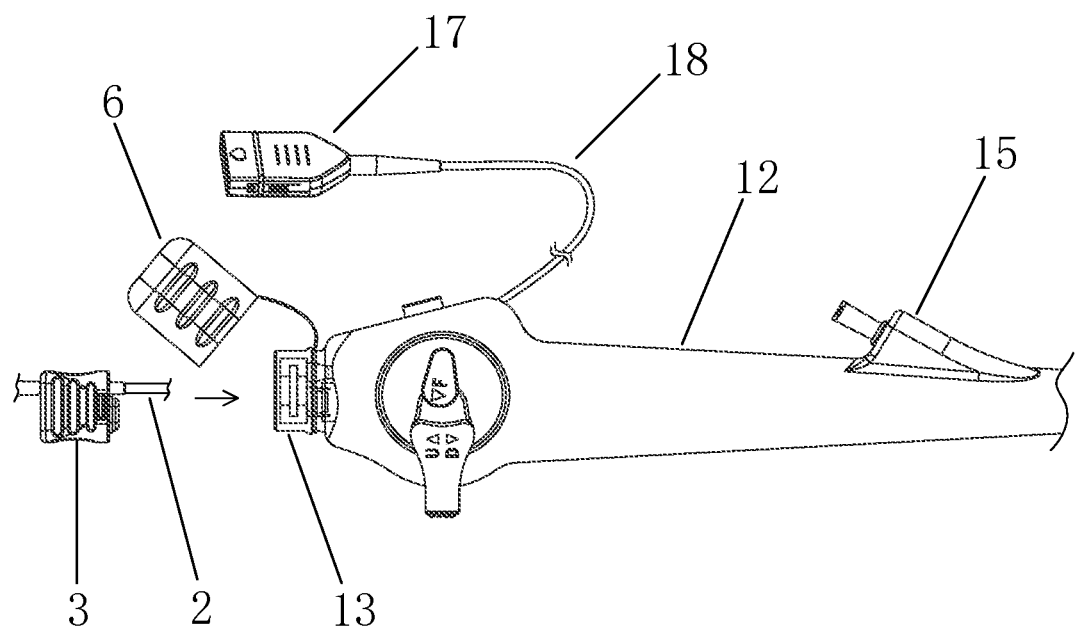
FIG. 7a is a structural diagram one of the soft endoscopy device according to an embodiment of the present invention.
Figure 7B:
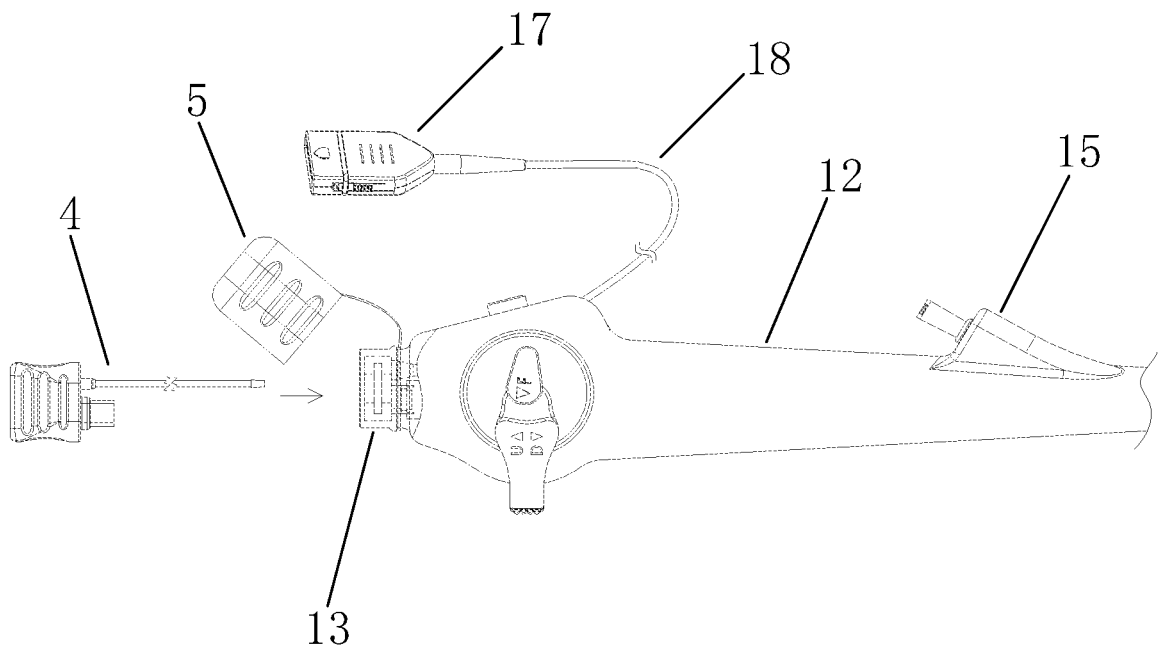
FIG. 7b is a structural diagram two of the soft endoscopy device according to an embodiment of the present invention.

Further, with reference to FIGS. 7a and 7b, the endoscope body structure 1 further includes an external connecting portion 17 located outside the handle portion 12, the electrical interface is directly or indirectly electrically connected with the external connecting portion, and when the camera assembly 4 is inserted into the first electrical interface, the camera assembly 4 is capable of transmitting electrical energy and/or a signal to the external connecting portion through the first electrical interface; in other words, an electrical path may be formed directly or indirectly among the camera assembly 4, the first electrical interface, the external connecting portion 17 and other external equipment, thereby transmitting the electrical energy and/or the electrical signals through the electrical path.

The transmission of electrical energy involved above may, for example, power the image acquisition components in the camera assembly 2; in a specific example, if the endoscope body structure, the camera assembly and the like are provided with the illumination module, the transmission of electrical energy also does not exclude the means of powering the lighting module, etc.; the transmission of the signal involved above may be, for example, the transmission of signals of CMOS images, or, for example, the transmission of control signals of the camera assembly 2.

In an embodiment, the endoscope body structure further includes a first circuit board (not shown) and a first electrical wire 18, the first circuit board being electrically connected with the first electrical interface, and the first circuit board being connected with the external connecting portion 17 via the first electrical wire to transmit the electrical energy and/or the signal by using the first electrical wire 18; and the first circuit board is located in the handle portion, and the first electrical wire 18 penetrates through a wire via disposed at the handle portion 12.

In the above solution, the electrical connection may be performed externally by the first electrical interface of the endoscope body structure and the external connecting portion and the like after the camera assembly accesses the first access port of the endoscope body structure, so that the camera assembly itself may not be directly electrically connected externally and further the camera assembly may be completely isolated sterilely, thereby effectively avoiding or reducing the security risks; meanwhile, since the electrical wire of the camera assembly is not required to pass through the sterile sheath, the difficulty in operation is further reduced.

With reference to FIGS. 7a and 7b, in an embodiment, the soft endoscopy device further includes a sterile isolation cover 6, wherein the sterile isolation cover 6 is configured to cover the first access port 13 after the camera assembly 4, the instrument adapter structure and the like accesses and is assembled to the first access port 13. Through the sterile isolation cover, the endoscope body structure 1 may be isolated internally. Meanwhile, in the embodiment of the present invention, a solution where the sterile isolation cover 6 is not included may be adopted.

In an embodiment, the camera assembly 2 includes a camera encapsulation portion 43, a conducting rod 44, a second grip 41, a second electrical interface 42 disposed at the second grip and a second electrical wire 45.

At least a part of a rod segment of the conducting rod 44 is bendable, one end of the conducting rod 44 is connected with the second grip 41, and the camera encapsulation portion 43 is disposed at the other end of the conducting rod 44; the second electrical wire 45 penetrates through the conducting rod 44 and the second grip 41, one end of the second electrical wire 45 is directly or indirectly connected with the camera encapsulation portion 43, and the other end of the second electrical wire is directly or indirectly connected with the second electrical interface 42.

When the camera assembly 4 accesses the first access port, the second electrical interface 42 is inserted into the first electrical interface in the handle portion 12, and the conducting rod extends into the first passage.

The first electrical wire and the second electrical wire involved above may refer to a single electrical wire, and may also include a plurality of same or different electrical wires; meanwhile, a solution where other devices are configured in the electrical wire may not be excluded.

In an embodiment, in the process of manufacturing the disposable endoscope structure, lengths of the first passage and the like are difficult to control accurately. Meanwhile, in the process of bending the disposable endoscope body structure, the passage may be stretched or compressed under different situations.

Therefore, based on the above two situations, the camera encapsulation portion 43 may be difficult to reach the pre-set position, e.g., may be difficult to accurately reach the end of the flexible inserting portion 11 to capture the image in front, which further directly affects or decreases the field-of-view angle size of the image and reduces the field of view. Thus, in the present embodiment, an elastic compensation structure 412 is further introduced; specifically, the second grip 41 includes a grip head 411 and the elastic compensation structure 412 disposed at the grip head 411.

One end of the elastic compensation structure 412 along an access direction of the camera assembly is directly or indirectly connected with the conducting rod 44, and the other end of the elastic compensation structure is directly or indirectly connected with the grip head 411, e.g., connected to the grip head 411 via a component cover 4122, so as to further realize the relative fixation of the positions. The grip head 411 is fixed relative to the handle portion 12 after the camera assembly 4 accesses and is assembled to the first access port; for example, a corresponding positioning structure may be configured in the handle portion 12, and the grip head 411 may be fixed to a position relative to the handle portion 12 through the positioning structure after being accessed.

The elastic compensation structure 412 is configured to directly or indirectly push the conducting rod 44 by using an elastic force after the camera assembly 4 accesses and is assembled to the first access port, so that the camera encapsulation portion 43 is located at an end of the flexible inserting portion, or may be understood to be located at the required position.

The elastic force produced by the elastic compensation structure 412 may be a force produced by a force deformation of the elastic component to overcome the deformation. If the elastic component is a spring, the deformation may be, for example, a stretch or a compression; or if the elastic component is an elastic sheet or other construction, the deformation may also be the movement of a part of components in the construction.

In actual implementation, the elastic compensation structure 412 includes an elastic component 4121 (e.g., a spring), a component cover 4122 and a component sleeve 4123, and a side wall of the grip head 411 close to the camera encapsulation portion (i.e., the side wall on the right of FIG. 8) is provided with an elastic-component through hole, wherein the elastic-component through hole may be used for a part of constructs in the elastic compensation structure 412 to penetrate through, and the elastic component 4121, the component cover 4122 and the component sleeve 4123 are all disposed in an inner cavity of the grip head 411; the elastic component 4121 is connected between the component cover 4122 and the component sleeve 4123 along the access direction.

Figure 8:
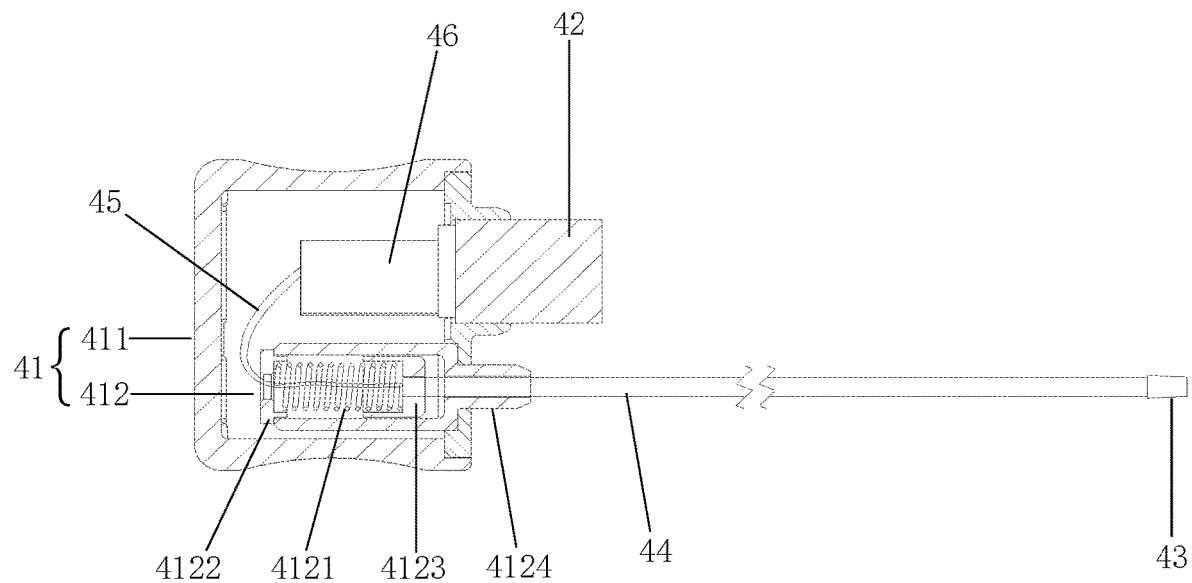
FIG. 8 is a structural diagram one of a camera assembly according to an embodiment of the present invention.
Figure 9:
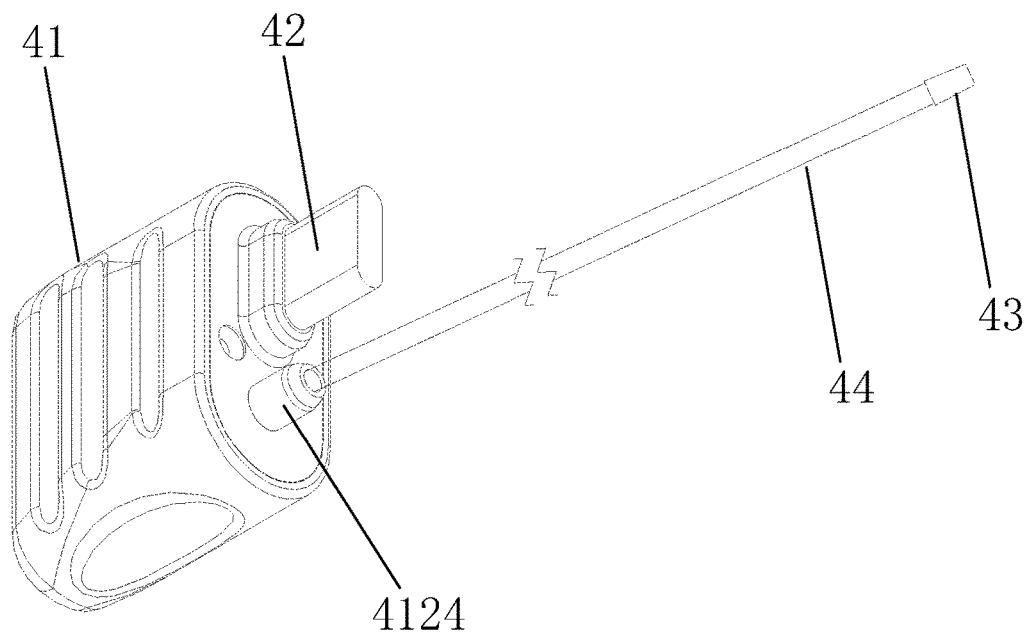
FIG. 9 is a structural diagram two of the camera assembly according to an embodiment of the present invention.
Figure 10:
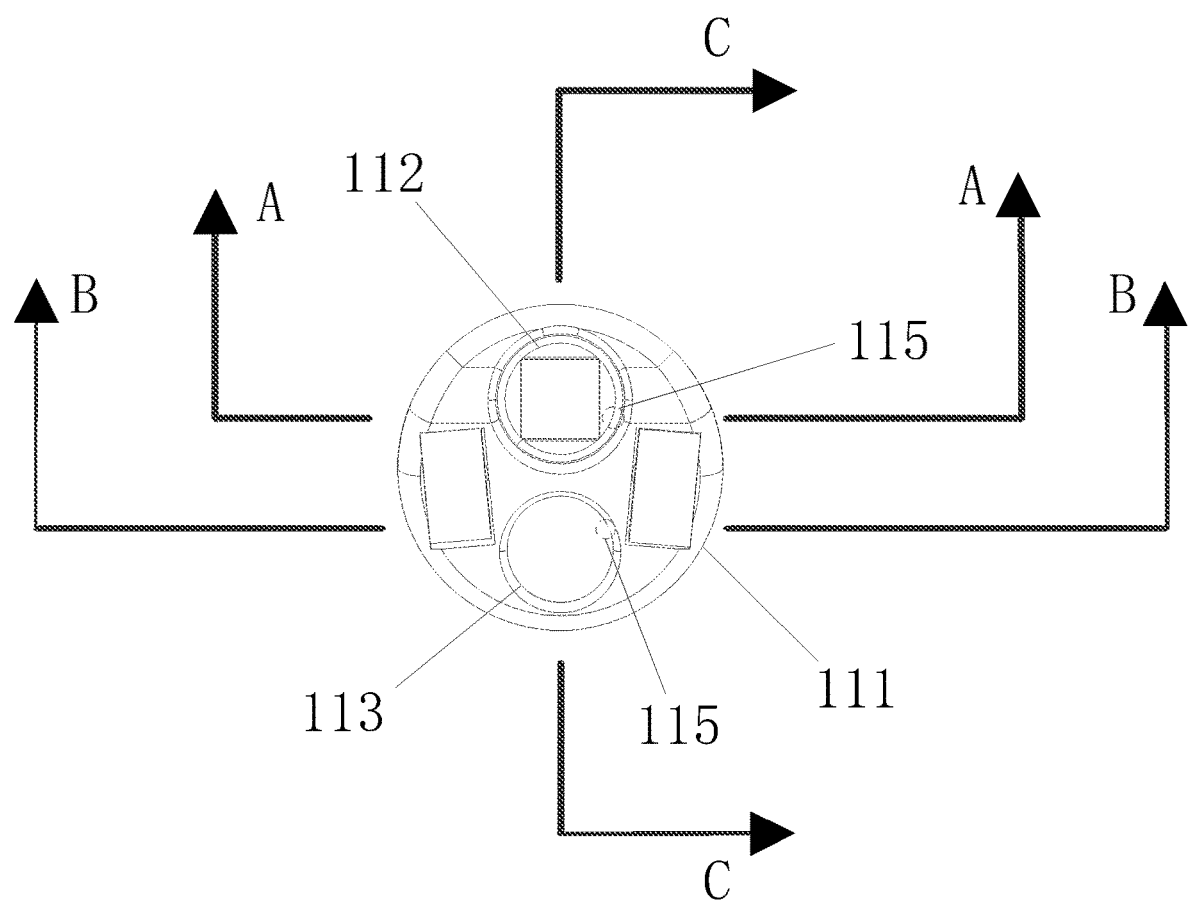
FIG. 10 is an end surface structural diagram of a head module, a first passage and a second passage according to an embodiment of the present invention.
Figure 11:
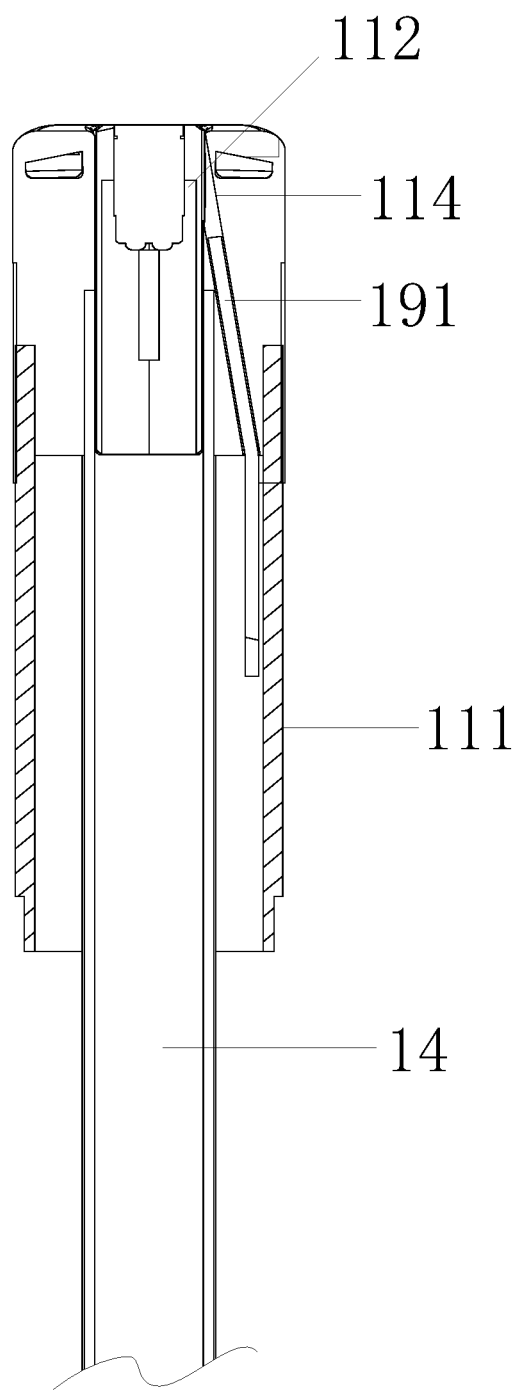
FIG. 11 is a partial structural diagram of A-A cross section in FIG. 1.
Figure 12:
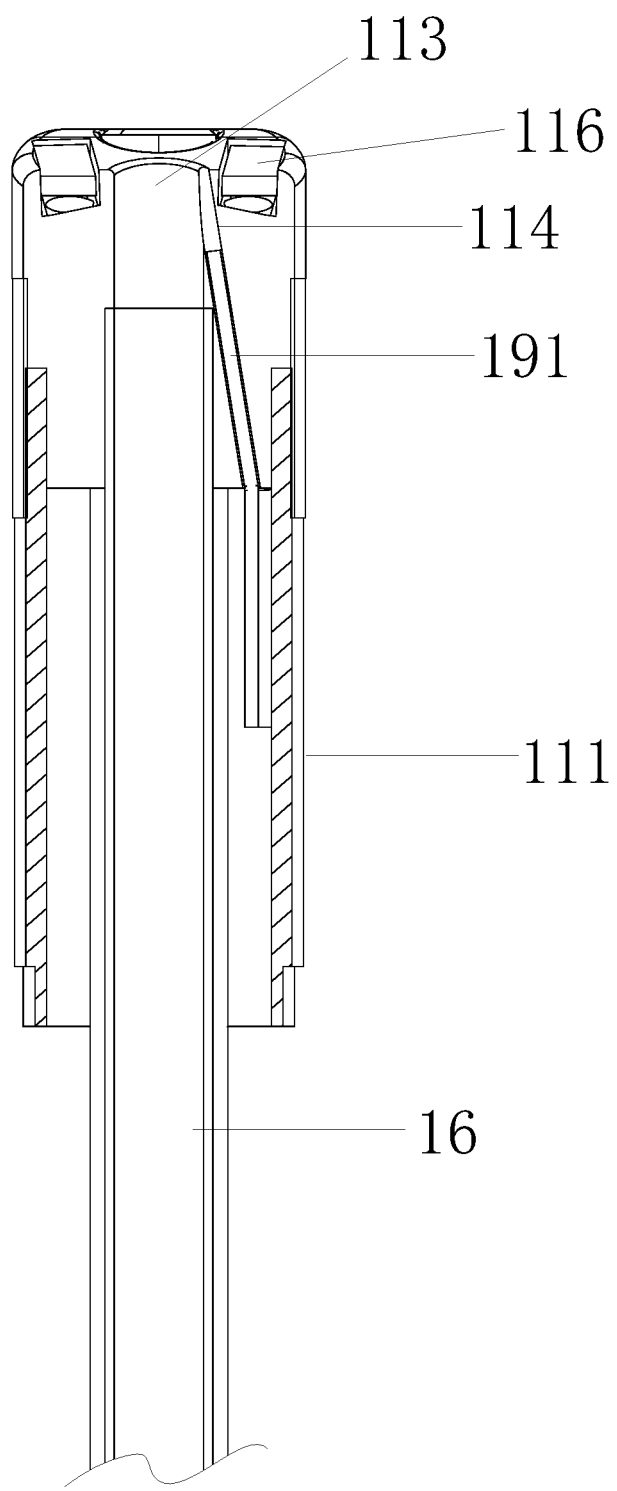
FIG. 12 is a partial structural diagram of B-B cross section in FIG. 1.

The second electrical wire 45 penetrates through the elastic-component through hole, the component sleeve 4123, and the component cover 4122 in sequence. As exemplified in FIG. 8, the second electrical wire 45 may pass through the elastic-component through hole, the component sleeve, and the component cover in sequence from the right to the left as shown in FIG. 8. The component sleeve 4123 is fixed relative to the conducting rod 44, e.g., may be fixedly connected to the latter; the component cover 4122 is fixed relative to the grip head 411, e.g., may be fixedly connected to the latter directly or indirectly.

In a further example, the elastic compensation structure 412 further includes a component seat 4124, the component seat penetrating through the elastic-component through hole, the component sleeve 4123 and the elastic component 4121 both being located at an inner side of the component seat 4124, and the component cover 4122 covering an end of the component seat 4124 deviated from a camera encapsulation portion 43; further, the component cover 4122 is fixed relative to the component seat 4124, and the component seat 4124 is fixed relative to the grip head 411.

With the above solution, based on the structure of resilience compensation, the encapsulation portion of the camera may be located at a required position by using the elastic force, thereby eliminating the effect caused by dimensional errors in manufacturing and assembly on the camera.

In a specific implementation process, the second electrical interface 42 and the elastic-component through hole are disposed at the same side wall of the grip head, and further accessing the grip head and docking the male connector with the receptacle (i.e., the first electrical interface and the second electrical interface) may be achieved by an accessing movement in the same direction.

The inner cavity of the grip head 411 is further provided with a second circuit board 46; the second circuit board 46 is fixed relative to the side wall, and the second electrical wire 45 is connected with the second electrical interface 42 via the second circuit board 46. In the above solution, the electrical connection is achieved based on the circuit board, so that the stability of the electrical connection may be effectively guaranteed.

In view of this, according to the present embodiment, the electrical connection may be achieved by inserting the electrical connectors, so that a positive effect of simple assembly may be generated; meanwhile, the disposable use and discarding of the electrical interfaces, the external connecting portion and the like may further generate a positive effect of facilitating the overall disposal.

The first electrical interface may be a receptacle, and the second electrical interface may be a male connector; in other examples, the second electrical interface may be the receptacle, and the first electrical interface may be the male connector.

In a specific example, the second electrical interface is a Type C male connector, and the first electrical interface is a Type C receptacle.

With reference to FIGS. 10 to 16, the flexible inserting portion 11 includes a bending rod (not shown), a head module 111 and an optical indication module 19 extending to the head module 111, one end of the bending rod being connected with the handle portion 12, and the other end of the bending rod being connected with the head module 111; both the first passage 14 and the second passage 16 for the second instrument to penetrate through the bending rod, and both the first passage 14 and the second passage 16 extend into the head module 111.

If the first passage 14 and the second passage 16 are formed by independent tube bodies respectively, the tube body may penetrate through the bending rod; correspondingly, the first passage 14 and the second passage 16 extending into the head module may refer to that the independent tube body extends into the head module. If the first passage 14 and the second passage 16 are formed in the bending rod, the two passages may be understood to penetrate through the passage cavity at two ends of the bending rod; correspondingly, the first passage 14 and the second passage 16 extending into the head module may refer to that the bending rod extends into the head module such that the two passages extend into the head module.

In an embodiment, the optical indication module 19 is configured to externally indicate a position of the instrument extending into the passage. In other words, the optical indication module externally indicates one of the following positions: the position of the first instrument extending into the first passage, the position of the camera assembly extending into the first passage, and the position of the second instrument extending into the second passage.

With reference to FIGS. 10 to 16, the head module 11 is internally provided with a first head passage 112, a second head passage 113, a lighting component 116 and at least one head optical fiber passage 114, the optical indication module 19 includes an illumination optical fiber 191 penetrating through the head optical fiber passage 114, and the handle portion 12 is provided with an observation window.

The first passage 14 is docked with an inlet of the first head passage 112, the second passage is docked with an inlet of the second head passage 113, and an optical import end of the head optical fiber passage 114 extends to the first head passage 112 or the second head passage 113.

In one example, a part of the head optical fiber passage 114 is connected with the first head passage 112, and a part of the head optical fiber passage is connected with the second head passage 113; in the other example, each of the head optical fiber passages is connected with the first head passage 112; in a further example, each of the head optical fiber passages is connected with the second head passage 113. In addition, the optical import end of the head optical fiber passage 114 may be connected to a front end or a position close to the front end of the corresponding head passage.

The lighting component 116 may, for example, be an LED, which may provide illumination for the regions in the front or the nearby regions. The light generated by the lighting component may enter the first head passage 112 and the second head passage 113 through a certain transmission path (for example, by one or more reflections), and then the optical signal may reach a first end of the illumination optical fiber via the optical import end of the head optical fiber passage.

The instrument accessing the first head passage 112 or the second head passage 113 may shield the optical import end of the corresponding head optical fiber passage 114; for example, the instrument accessing the first head passage 112 may shield the optical import end of the head optical fiber passage 114 connected to the first head passage 112; the instrument accessing the second head passage 113 may shield the optical import end of the head optical fiber passage connected to the second head passage 113.

When one end of the head optical fiber passage 114 is not shielded by the accessed instrument, a first end of the illumination optical fiber 191 is capable of collecting an optical signal directly or indirectly transmitted by the lighting component (e.g., an optical signal generated by more reflections); the illumination optical fiber 191 is further capable of conducting the optical signal to a second end of the illumination optical fiber, and the second end of the illumination optical fiber 191 extends into the handle portion 12 and is located at an inner side of the observation window.

The observation window may be any structure or material suitable for direct or indirect observation by human eyes and equipment. In a further example, the observation window may be arranged at a position matched with the entrances of the first passage and the second passage.

In the above solution, by the illumination optical fiber and the corresponding head optical fiber passage, the introduction and the conduction of the optical signals may be realized; further, by observing through the observation window, a situation where whether the instrument is inserted into the corresponding position of the head module may be observed, wherein specifically, it is indicated that the optical import end of the head fiber optical passage has not been shielded and then it can be considered that the corresponding instrument has not been inserted in place when exported optical signals are observed, and it is indicated that the optical import end of the head fiber optical passage has been shielded and then it can be considered that the corresponding instrument has been inserted in place (or substantially inserted into place) when exported optical signals are not observed (or the observed light is weak).

It should be further noted that in the scenario of the embodiment of the present invention, when the double instruments are accessed, there is a lack of images fed back by the camera assembly, and then the feedback of the positions of the instruments is particularly important, which can help to achieve precise control of the positions of the instruments and ensure that the corresponding operation is performed after the instrument is in place.

Figure 13:
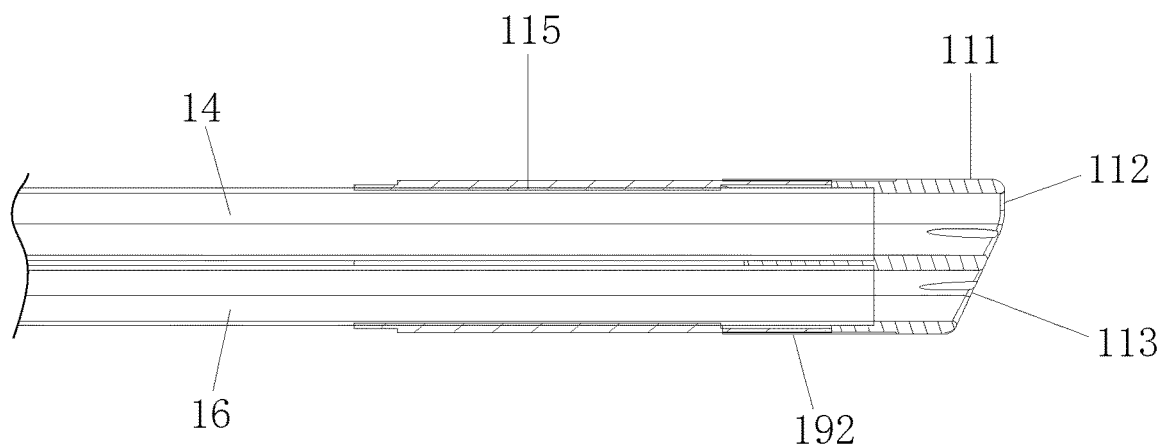
FIG. 13 is a partial structural diagram of C-C cross section in FIG. 1.
Figure 14:
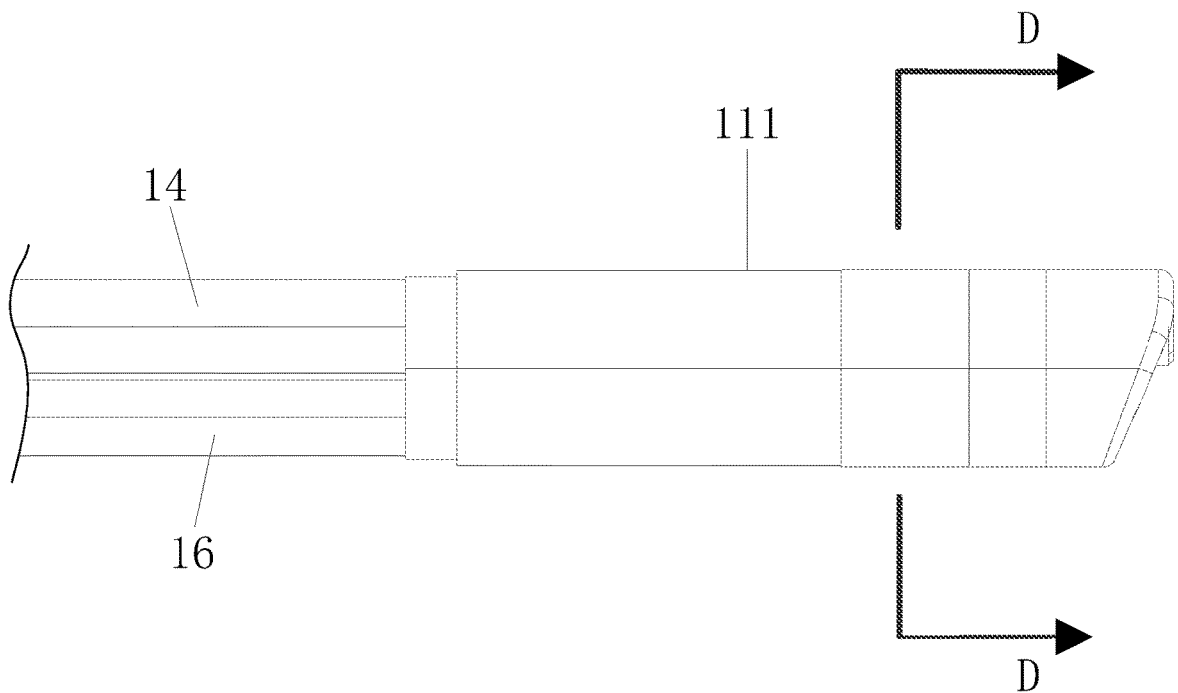
FIG. 14 is a side surface structural diagram one of a head module, a first passage and a second passage according to an embodiment of the present invention.
Figure 15:
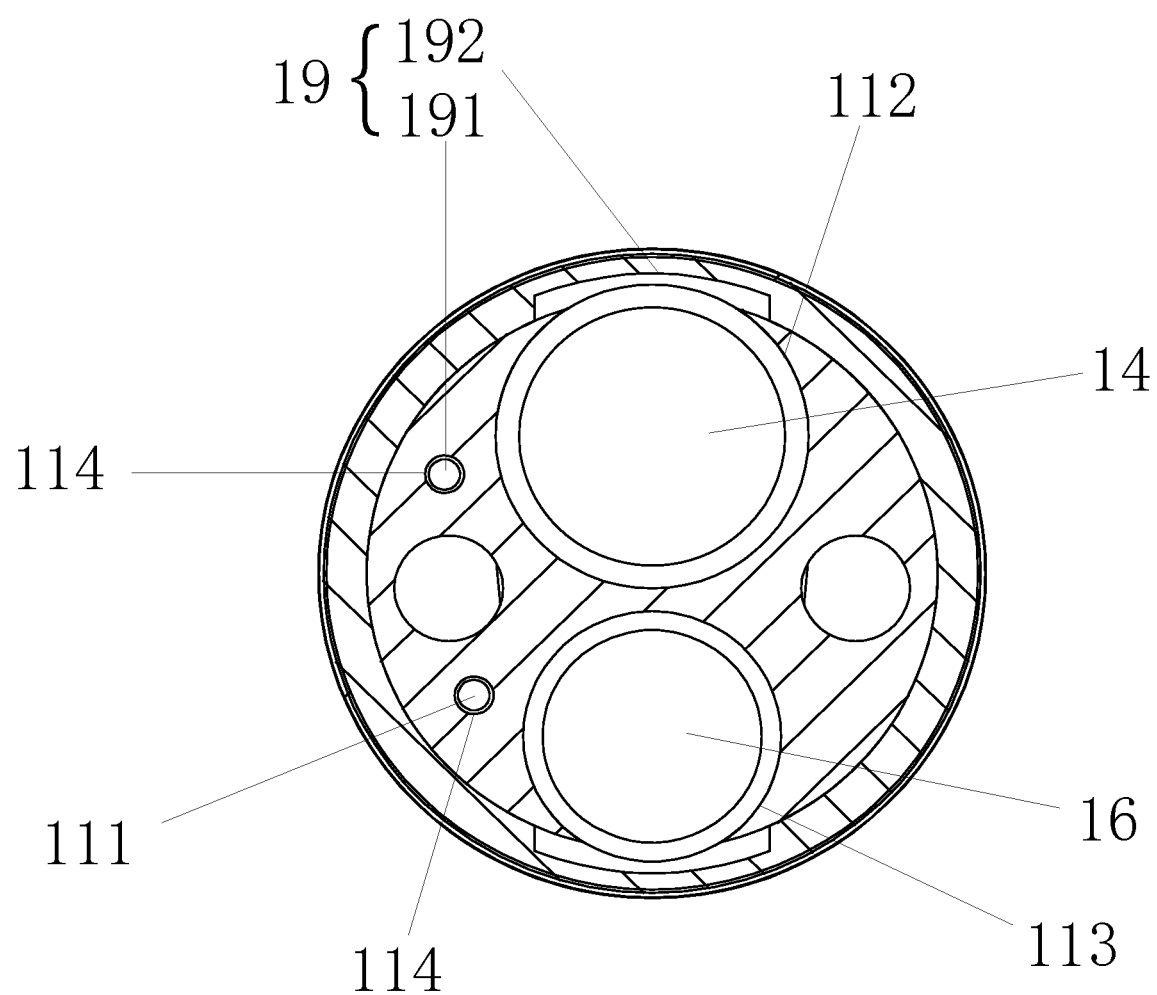
FIG. 15 is a partial structural diagram of D-D cross section in FIG. 14.
Figure 16:
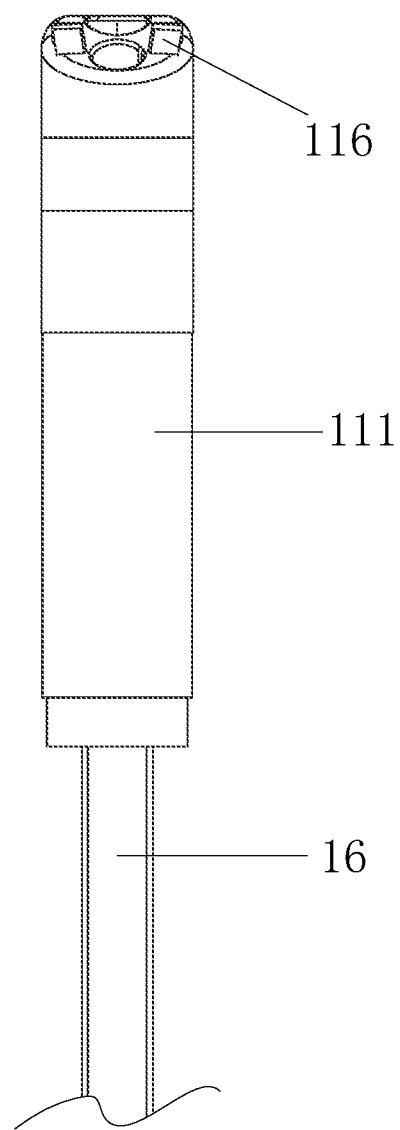
FIG. 16 is a side surface structural diagram two of the head module, the first passage and the second passage according to an embodiment of the present invention.

In a specific example, with reference to FIG. 13, in the head module 11, a rear end accommodation cavity 115 may be formed, wherein the rear end accommodation cavity may be configured for the first passage 14 and the second passage 16 to insert into, and the rear end accommodation cavity 115 may be connected to rear ends of the first head passage 112 and the second head passage 113, so that further the accessed first passage 14 and the accessed second passage 16 may be matched and docked with the first head passage and the second head passage.

In practice, the illumination optical fiber used may be two illumination optical fibers, wherein one end of the optical fiber accesses to the exit of the passage in the head module, and the other end thereof accesses to the handle portion; when the instrument reaches the tip when being inserted into the passage, the reflected light of the illumination module (i.e., the light component mentioned above) will be shielded, and the purpose of feeding back the positions may be achieved by observing the changes in the brightness of the indicated light.

Moreover, compared with the solution where the lighting component is required to be disposed partially in the camera assembly, the camera assembly may not be required to be provided with the lighting component due to the provision of the lighting component in the head module, which may help make the size of the outer diameter smaller.

At last, it should be noted that the above various embodiments are only used to describe the technical solutions of the present invention, rather than limiting the technical solutions of the present invention. Even though the present invention is described in detail with reference to the foregoing embodiments, those of ordinary skilled in the art should understand that they can still modify the technical solutions recorded in the foregoing various embodiments or equivalently replace some or all of the technical features. However, these modifications or replacements do not make the essence of the corresponding technical solutions deviate from the scope of the technical solutions of the embodiments of the present invention.

What is claimed is:

1. A soft endoscopy device, comprising an endoscope body structure, a camera assembly and an instrument adapter structure, wherein the endoscope body structure comprises a bendable flexible inserting portion and a handle portion connected to one end of the flexible inserting portion, the handle portion being provided with a first access port, and the flexible inserting portion being internally provided with a first passage; the first access port being directly or indirectly connected with the first passage;
   the first access port being matched with the camera assembly, and when the camera assembly accesses the first access port, at least part of the camera assembly extending into the first passage;
   the first access port being further matched with the instrument adapter structure, and when the instrument adapter structure accesses the first access port and the instrument adapter structure is equipped with a first instrument, the first instrument extending into the first passage;
   the handle portion is further provided with a second access port for accessing a second instrument, a second passage for the second instrument to extend into penetrating through the flexible inserting portion, and the second access port being directly or indirectly connected with the second passage;
   the flexible inserting portion comprises a bending rod, a head module and an optical indication module extending to the head module, one end of the bending rod being connected with the handle portion, and the other end of the bending rod being connected with the head module; both the first passage and the second passage for the second instrument to penetrate through penetrating through the bending rod, and both the first passage and the second passage extending into the head module; and the optical indication module being used to externally indicate a position of the instrument extending into the passage;
   the head module is internally provided with a first head passage, a second head passage, a lighting component and at least one head optical fiber passage, the optical indication module comprising an illumination optical fiber, and the handle portion being provided with an observation window;
   the first passage being docked with an inlet of the first head passage, the second passage being docked with an inlet of the second head passage, an optical import end of the head optical fiber passage extending to the first channel of the first head passage or the second head passage, and an instrument accessing the first head passage or the second head passage being capable of shielding the optical import end of the corresponding head optical fiber passage; and
   the illumination optical fiber penetrating through the head optical fiber passage; when the optical import end is not shielded, a first end of the illumination optical fiber being capable of collecting an optical signal directly or indirectly transmitted by the lighting component; the illumination optical fiber further being capable of conducting the optical signal to a second end of the illumination optical fiber, and the second end of the illumination optical fiber extending into the handle portion and located at an inner side of the observation window.

2. The soft endoscopy device according to claim 1, wherein the instrument adapter structure comprises a first grip, and the first grip being internally provided with an instrument passage for the first instrument to penetrate through.

3. The soft endoscopy device according to claim 2, wherein the camera assembly comprises a camera encapsulation portion, a conducting rod, a second grip, a second electrical interface disposed at the second grip and a second electrical wire,
- at least a part of a rod segment of the conducting rod being bendable, one end of the conducting rod being connected with the second grip, and the camera encapsulation portion being disposed at the other end of the conducting rod; the second electrical wire penetrating through the conducting rod and the second grip, one end of the second electrical wire being directly or indirectly connected with the camera encapsulation portion, and the other end of the second electrical wire being directly or indirectly connected with the second electrical interface; and
- when the camera assembly accesses the first access port, the second electrical interface being inserted into the first electrical interface in the handle portion, and the conducting rod extending into the first passage.

4. The soft endoscopy device according to claim 1, wherein the handle portion is further internally provided with a first electrical interface; when the camera assembly accesses the handle portion internally, the camera assembly is conductively inserted into the first electrical interface; and
- the instrument adapter structure is provided with an electrical interface protective portion; when the instrument adapter structure accesses the handle portion internally, the electrical interface protective portion is docked with the first electrical interface.

5. The soft endoscopy device according to claim 4, wherein the endoscope body structure further comprises an external connecting portion located outside the handle portion, the electrical interface being directly or indirectly electrically connected with the external connecting portion, and when the camera assembly is inserted into the first electrical interface, the camera assembly being capable of transmitting electrical energy and/or a signal to the external connecting portion through the first electrical interface.

6. The soft endoscopy device according to claim 5, wherein the endoscope body structure further comprises a circuit board and a first electrical wire, the circuit board being electrically connected with the first electrical interface, and the circuit board being connected with the external connecting portion via the first electrical wire to transmit the electrical energy and/or the signal by using the first electrical wire; and the circuit board being located in the handle portion, and the first electrical wire penetrating through a wire via disposed at the handle portion.

7. The soft endoscopy device according to claim 6, wherein the camera assembly comprises a camera encapsulation portion, a conducting rod, a second grip, a second electrical interface disposed at the second grip and a second electrical wire,
- at least a part of a rod segment of the conducting rod being bendable, one end of the conducting rod being connected with the second grip, and the camera encapsulation portion being disposed at the other end of the conducting rod; the second electrical wire penetrating through the conducting rod and the second grip, one end of the second electrical wire being directly or indirectly connected with the camera encapsulation portion, and the other end of the second electrical wire being directly or indirectly connected with the second electrical interface; and
- when the camera assembly accesses the first access port, the second electrical interface being inserted into the first electrical interface in the handle portion, and the conducting rod extending into the first passage.

8. The soft endoscopy device according to claim 5, wherein the camera assembly comprises a camera encapsulation portion, a conducting rod, a second grip, a second electrical interface disposed at the second grip and a second electrical wire,
- at least a part of a rod segment of the conducting rod being bendable, one end of the conducting rod being connected with the second grip, and the camera encapsulation portion being disposed at the other end of the conducting rod; the second electrical wire penetrating through the conducting rod and the second grip, one end of the second electrical wire being directly or indirectly connected with the camera encapsulation portion, and the other end of the second electrical wire being directly or indirectly connected with the second electrical interface; and
- when the camera assembly accesses the first access port, the second electrical interface being inserted into the first electrical interface in the handle portion, and the conducting rod extending into the first passage.

9. The soft endoscopy device according to claim 4, wherein the camera assembly comprises a camera encapsulation portion, a conducting rod, a second grip, a second electrical interface disposed at the second grip and a second electrical wire,
- at least a part of a rod segment of the conducting rod being bendable, one end of the conducting rod being connected with the second grip, and the camera encapsulation portion being disposed at the other end of the conducting rod; the second electrical wire penetrating through the conducting rod and the second grip, one end of the second electrical wire being directly or indirectly connected with the camera encapsulation portion, and the other end of the second electrical wire being directly or indirectly connected with the second electrical interface; and
- when the camera assembly accesses the first access port, the second electrical interface being inserted into the first electrical interface in the handle portion, and the conducting rod extending into the first passage.

10. The soft endoscopy device according to claim 1, wherein the camera assembly comprises a camera encapsulation portion, a conducting rod, a second grip, a second electrical interface disposed at the second grip and a second electrical wire,
- at least a part of a rod segment of the conducting rod being bendable, one end of the conducting rod being connected with the second grip, and the camera encapsulation portion being disposed at the other end of the conducting rod; the second electrical wire penetrating through the conducting rod and the second grip, one end of the second electrical wire being directly or indirectly connected with the camera encapsulation portion, and the other end of the second electrical wire being directly or indirectly connected with the second electrical interface; and
- when the camera assembly accesses the first access port, the second electrical interface being inserted into the first electrical interface in the handle portion, and the conducting rod extending into the first passage.

11. The soft endoscopy device according to claim 10, wherein the second electrical interface is a Type C male connector, and the first electrical interface is a Type C receptacle.

* * * * *